(12) United States Patent
Miller, III

(10) Patent No.: US 6,238,387 B1
(45) Date of Patent: May 29, 2001

(54) ELECTROSURGICAL GENERATOR

(75) Inventor: Scott A. Miller, III, Boulder, CO (US)

(73) Assignee: Team Medical, L.L.C., Boulder, CO (US)

( * ) Notice: Subject to any disclaimer, the term of this patent is extended or adjusted under 35 U.S.C. 154(b) by 0 days.

(21) Appl. No.: 09/192,746

(22) Filed: Nov. 16, 1998

Related U.S. Application Data

(63) Continuation of application No. 08/702,282, filed on Aug. 23, 1996, now Pat. No. 5,836,943.

(51) Int. Cl.$^7$ .................................................. A61B 18/18
(52) U.S. Cl. ............................................. 606/34; 606/42
(58) Field of Search .......................... 606/32–35, 38–42; 607/101, 102

(56) References Cited

U.S. PATENT DOCUMENTS

| | | |
|---|---|---|
| 3,900,823 | 8/1975 | Sokal et al. . |
| 3,919,656 | 11/1975 | Sokal et al. . |
| 4,184,197 | 1/1980 | Cuk et al. . |
| 4,186,437 | 1/1980 | Cuk . |
| 4,257,087 | 3/1981 | Cuk . |
| 4,274,133 | 6/1981 | Cuk et al. . |
| 4,658,819 * | 4/1987 | Harris et al. ............................ 606/34 |
| 5,078,078 | 1/1992 | Cuk . |
| 5,318,563 | 6/1994 | Malis et al. . |
| 5,370,645 * | 12/1994 | Klicek et al. ........................... 606/35 |
| 5,416,387 | 5/1995 | Cuk et al. . |
| 5,442,534 | 8/1995 | Cuk et al. . |
| 5,442,539 | 8/1995 | Cuk et al. . |
| 5,472,443 | 12/1995 | Cordis et al. . |
| 5,496,312 * | 3/1996 | Klicek .................................... 606/34 |
| 5,539,630 | 7/1996 | Pietkiewicz et al. . |
| 5,540,681 | 7/1996 | Strul et al. . |
| 5,556,396 * | 9/1996 | Cohen et al. ........................... 606/42 |
| 5,570,276 | 10/1996 | Cuk et al. . |
| 5,630,426 * | 5/1997 | Eggers et al. ......................... 128/734 |
| 5,633,578 | 5/1997 | Eggers et al. . |
| 5,800,426 * | 9/1998 | Taki et al. .............................. 606/32 |
| 5,817,093 * | 10/1998 | Williamson, IV et al. ............. 606/50 |
| 5,957,922 * | 9/1999 | Imran .................................... 606/41 |
| 6,016,452 * | 1/2000 | Kasevich .............................. 607/101 |

* cited by examiner

*Primary Examiner*—Michael Peffley
(74) *Attorney, Agent, or Firm*—Marsh Fischmann & Breyfogle LLP

(57) ABSTRACT

An electrosurgical generator is disclosed that provides radio-frequency electrical waveforms for performing surgical operations on a tissue mass. The various aspects of the present invention are embodied in an electrosurgical generator that includes a DC regulator, an amplifier, an energy recovery circuit, and a method of controlling these components to generate a desired electrical waveform for an electrosurgical operation.

20 Claims, 5 Drawing Sheets

ELECTROSURGICAL GENERATOR

REFERENCE TO RELATED PATENT APPLICATIONS

This application is a continuation of U.S. patent application Ser. No. 08/702,282 entitled "IMPROVED ELECTROSURGICAL GENERATOR" filed Aug. 23, 1996, now U.S. Pat. No. 5,836,943, which prior application is hereby incorporated by reference in its entirety.

FIELD OF THE INVENTION

This invention relates to electrosurgical generators in general and, in particular, to an improved electrosurgical generator capable of supplying a plurality of radio frequency electrical waveforms for surgical procedures.

BACKGROUND

Electrosurgery involves the application of radio-frequency electrical energy to tissue to produce a surgical operation. Electrosurgery is generally performed with a generator that converts electrical energy from a power source to a predetermined radio-frequency waveform that is delivered to the tissue through an active electrode and a return path.

There are essentially four main surgical operations that are electrically performed on tissue, depending on the radio-frequency waveform output by the generator. These operations are typically described as desiccation, fulguration, cutting and cutting with hemostasis.

For a desiccation operation, the generator outputs a radio-frequency waveform that heats the tissue, by electrical resistance heating due to current flowing through the tissue, sufficient to produce an area of necrosis.

For a fulguration operation, the generator typically outputs a burst waveform which has a high peak voltage but a low duty cycle. Due to the low duty cycle of the fulgurating waveform, the power per unit time applied to the tissue is low enough so that explosive vaporization of cell moisture is minimized. The burst waveform forms a radio-frequency spark or arc between the active electrode and the tissue, thereby delivering power over the area of the spark or arc tissue contact and providing coagulation of the tissue in the immediate vicinity of the spark or arc.

Other operations can be performed with still different waveforms output by an electrosurgical generator. Cutting occurs when sufficient power per unit time is delivered to the tissue to vaporize cell moisture. Cutting is typically performed with a repetitive voltage waveform, such as a sinusoid, which produces a cut with very little necrosis and little hemostasis.

It is also possible to achieve a combination of the above operations by varying the electrical waveform produced by the generator. In particular, a combination of cutting and desiccation (called cutting with hemostasis or blend) can be produced by periodically interrupting the continuous sinusoidal voltage normally used to produce an electrosurgical cut.

Known electrical generators which are capable of producing one or more of the above-described surgical operations are generally designed as in FIG. 1. The AC power mains 200 provide AC electrical power to AC/DC converter 202, which provides unregulated DC power to the DC regulator 206. Under the control of clinician 208, control and timing circuitry 210 causes the DC regulator 206 to produce DC power of a specified value to the tuned RF amplifier 212. The control and timing circuitry 210 also produces RF signals for amplification by the tuned RF amplifier 212. This results in RF power signals being delivered to the patient 214.

Known electrosurgical generators are subject to one or more limitations. For example, some generators are limited in the degree to which they can generate more than one individual waveform without producing an admixture of inappropriate effects, thus they are limited in the number of electrical waveforms that are appropriate for surgical operations.

Another limitation is that known generators emit a substantial amount of electromagnetic interference to the environment. Electromagnetic interference poses a serious risk in operating rooms where it can cause malfunction or failure of electronic equipment. A primary source of the electromagnetic interference is the substantial pulsating currents which are created in electrosurgical generators circuits.

There are primarily two sources of electromagnetic interference (EMI) in known generators. Such EMI consists of conducted EMI, nearfield EMI and radiated EMI. A primary source of the conducted EMI, which is sent back into the AC power lines and carried to equipment at distant locations in the hospital and beyond, is produced by the substantially pulsating currents which are created in the DC regulator 206. A primary source of the nearfield and radiated EMI is the harmonic content of the tuned amplifier output. The harmonic components couple much better to the environment, and are radiated away more effectively. As will be shown, a key aspect of this invention is the simultaneous reduction of conducted, nearfield and radiated EMI.

Another limitation of known electrosurgical generators is their relatively low efficiency in converting and amplifying electrical power from the power source to the tissue, resulting in the dissipation of electrical energy as heat. Heat dissipation by an electrosurgical unit (ESU) within an operating room is objectionable due to the generation of convective air currents and the associated circulation of airborne pathogens. The additional heat dissipation requirement increases the weight and volume of the ESU. Furthermore, the reliability of the electrosurgical unit typically decreases as the heat dissipation increases.

Low efficiency in ESU's are caused by a number of effects:

(1) Topology selected, which determines intrinsic efficiency (maximum achievable efficiency under optimum conditions);

(2) Loading, which determines extrinsic efficiency (efficiency achieved with given topology into a given load);

(3) Component selection, which determines realized efficiency (efficiency with a given topology, load and selection of components).

Ideally, a topology is selected which maximizes the extrinsic and realized efficiency over a wide range of conditions. In known ESU's, in order to achieve cutting with a minimum of hemostasis, AC ripple voltage present on the DC regulator output should be minimized. At the same time, the conducted EMI should be reduced as much as possible. To do this, large size capacitors are sometimes added to the AC/DC convertor 202, in FIG. 1, in an attempt to smooth the current pulses, reducing conducted EMI, while at the same time large capacitors are added to the output of the DC regulator 206 to reduce output ripple and hence reduce hemostasis. These capacitors filter the current by passing the ripple component to ground through the ESR of the capacitor, thereby wasting power. This loss and bulk would be greatly reduced if less AC ripple were generated, and hence less power wasted.

Control devices, such as transistors, are often used in both the DC regulator 206 and the RF amplifier 212 circuits to synthesize and regulate the electrical waveform applied to tissue. These control devices may be used in a variety of ways. A very common method in prior art has been to use the control devices as variable impedance current sources which results in the simultaneous application of voltage and current across the transistor and thereby a dissipation of power within the transistor. Control devices are also used as alternating low impedance (i.e., closed) and high impedance (i.e., open) switches. In prior art, some generator circuits dissipate a substantial amount of power in such switches due to transitioning the switches to low impedance while a voltage exists across the switch and thereby dissipating power due to the simultaneous presence of voltage and current in the switch. Some topologies of generator circuits which contain transistors often cannot tie the biasing of the transistors to a common reference node, thereby requiring relatively complicated level shifting circuitry.

Some known electrosurgical generators' topologies convert the input voltage to an output voltage through a process that includes storing input energy inductively in the form of a DC magnetic field during one interval and releasing the energy as an oscillating voltage across a load during a subsequent interval. This process of storage and release of energy results in a waveform in the form of a damped sinusoid which has a significant amplitude remaining at the time of the next storage cycle. For some output waveforms, such as pulsed energy waveforms, energy not sent to the load by the end of the pulse remains in the generator where it is dissipated as heat, decreasing the generator's efficiency.

Consequently, there is a need for a generator that addresses such limitations of known electrosurgical generators.

SUMMARY OF THE INVENTION

Accordingly, objectives of the present invention include the following:

To provide an electrosurgical generator with reduced generation of electromagnetic interference.

To provide an electrosurgical generator with improved efficiency.

To provide an electrosurgical generator with current isolation between an input power source and an output load.

To provide an electrosurgical generator with a reduced number and size of electrical components.

To provide a switching DC regulator for an electrosurgical generator wherein input and output current ripple is substantially reduced.

To provide a switching DC regulator for an electrosurgical generator with an adjustable output DC voltage that can be increased (step-up) or decreased (step-down) relative to the input DC voltage.

To provide an amplifier for an electrosurgical generator that converts a DC input voltage to a radio-frequency signal that provides surgical effects on tissue with reduced generation of electromagnetic interference and increased efficiency.

To provide an energy recovery circuit for an electrosurgical generator that selectively stores and releases energy within the generator to increase the efficiency of energy delivery to the tissue.

To provide an electrosurgical generator whereby the flow of energy to the tissue is controlled in response to a sensed tissue condition to provide improved surgical effects.

One or more of the above objectives are addressed by providing a generator that comprises an inventive DC regulator, amplifier, and energy recovery circuit. These generator components can be controlled in an inventive manner to convert energy from a power source to a range of predetermined radio-frequency waveforms to provide electrosurgical operations, e.g., desiccation, fulguration, cutting, or cutting with hemostasis.

The DC regulator and the amplifier are connected in series between a power source (e.g., a battery or AC-to-DC converter) and the tissue. Generally, the power source provides a DC voltage to the DC regulator. The DC regulator converts the input DC voltage to a range of DC output voltages that can be greater (step-up) or lesser (step-down) than the DC input voltage. The DC output voltage flows into the amplifier where it is converted to a range of radio-frequency voltage waveforms which are delivered to the tissue. The energy recovery circuit stores and releases energy generated by the amplifier to increase the efficiency with which energy is transferred from the power source to the tissue.

According to one aspect of the invention, an inventive switched DC regulator is provided that achieves increased efficiency, a reduced generation of electromagnetic interference, and a reduced number of circuit components. The switched DC regulator converts a first DC signal from a power source into a second DC signal having a predetermined voltage.

The switched DC regulator includes an input inductor means (e.g., one or more inductors) for reducing current ripple in the first DC signal, capacitor means (e.g., one or more capacitors) for capacitively storing and releasing energy, first switch means (e.g., bipolar transistor, diode, insulated gate bipolar transistor, or field effect transistor) for alternately charging the capacitor means with the first DC signal and second switch means for discharging the capacitor means to generate the second DC signal, and output inductor means (e.g., one or more inductors) for reducing current ripple in the second DC signal.

The input inductor means is connected in series between the power source and the capacitor means. The capacitor means is connected in series between the input inductor means and the output inductor means. Energy is capacitively transferred from the input inductor means to the output inductor means by the first switch means charging the capacitor means with the first DC signal and the second switch means discharging the capacitor means through the output inductor means to generate the second DC signal. The voltage of the second DC signal is controlled by adjusting the duty ratio of the first and second switch means, i.e., adjusting the ratio of the time that the capacitor means is charged to the total time over which the capacitor means is charged and discharged. The second DC signal voltage can be higher (step-up) or lower (step-down) than the first DC signal voltage.

The current ripples in the first DC signal and the second DC signal are further reduced by properly magnetically coupling the input inductor means and the output inductor means. Proper magnetic coupling is achieved by considering the coefficient of coupling K and the turns ratio N of a transformer. Moreover, proper magnetic coupling occurs when K substantially equals N for the transformer. Such substantial equivalence may be obtained either by using a transformer designed such that K is substantially equal to N or by using a transformer in conjunction with one or more auxiliary inductances, such auxiliary inductances selected so that K is substantially equal to N. DC isolation between the first DC signal and the second DC signal is achieved by the capacitor means including a first and a second capacitor with an isolation transformer interposed between the capacitors. Current ripples in the first DC signal and the second DC signal are substantially reduced to zero by magnetically coupling the input and output inductor means and the isolation transformer.

The efficiency of the DC regulator is substantially improved by selecting the input inductor means, the output inductor means, and the capacitor means to provide a substantially zero voltage across the switch means and a substantially zero instantaneous rate of change of voltage across the switch means prior to the switch means closing to charge the capacitor means. In this manner, energy dissipation in the switch means is substantially eliminated by avoiding the simultaneous application of a voltage across the switch means and a current through the switch means.

According to another aspect of the present invention, an inventive amplifier is provided that converts the second DC signal generated by the DC regulator into a radio-frequency output signal having a predetermined frequency appropriate for achieving electrosurgical effects. The inventive amplifier yields increased efficiency and a reduced generation of electromagnetic interference.

The amplifier includes input inductor means in series with the DC regulator or another DC source (e.g., AC-to-DC converter, or battery), a resonant circuit connected in series with the input inductor means, and switch means in parallel with the resonant circuit. The input inductor means reduces the current ripple in the second DC signal and thereby reduces the radiated electromagnetic interference. The resonant circuit includes an inductor, a capacitor, and the tissue. The switch alternately connects (closed switch) and disconnects (open switch) a junction between the input inductor and the resonant circuit to a current return path for the amplifier, thereby periodically charging the resonant circuit with the second DC signal and discharging energy as the output signal. The magnitude and frequency of the output signal is regulated by adjusting the duty ratio and period of the switch, i.e., adjusting the ratio of the time that the resonant circuit is charged to the total time over which the resonant circuit is charged and discharged.

The components of the resonant circuit are selected to provide a substantially zero voltage and zero rate of change of voltage across the switch prior to the switch closing to charge the input inductor. In this manner, energy dissipation in the switch is substantially eliminated by avoiding the simultaneous application of a voltage potential across the switch and a current through the switch, and the sensitivity of the amplifier circuit to component tolerances is substantially reduced.

According to another aspect of the present invention, an energy recovery circuit is provided for use in an electrosurgical generator that improves the efficiency of energy delivery to the tissue. An electrosurgical generator synthesizes varying width bursts/waveforms of radio-frequency energy to create the various types of surgical operations. At the end of a burst type output signal, the energy that has not been delivered to the tissue remains within the generator where it is dissipated as heat. The energy dissipated within the generator can be quite high when the resistance of the tissue is relatively high. The energy recovery circuit substantially reduces these loses by recovering the energy remaining within the electrosurgical generator at the end of a burst/ waveform. The energy recovery circuit generally includes an energy storage device(s) (e.g., capacitor, inductor, or combination thereof), a switch(es) (e.g., bipolar transistor, insulated gate bipolar transistor, or field effect transistor) that alternatively stores and releases energy between the energy storage device(s) and the electrosurgical generator, and a switch controller that regulates the storing and release of energy.

Generally, to reduce the energy lost at the end of a burst output signal, the switch controller toggles the switch to alternately store energy in the energy recovery circuit near the end of a burst and then to release the stored energy during a subsequent burst. In this manner, the energy can be selectively stored and later released to increase the efficiency of energy transfer to the tissue. As can be appreciated, the energy recovery circuit can be controlled to store and release energy at any time and is thereby not limited to storing energy at any time and is thereby not limited to storing energy at particular times, such as near the end of a burst output signal.

According to another aspect of the present invention, a method for operating an electrosurgical unit is provided whereby the flow of energy to the tissue is controlled in response to a sensed tissue condition to provide improved surgical effects, e.g., desiccation, fulguration, cutting, or cutting with hemostasis. It has been found that the complex impedance of tissue provides information about the condition of the tissue and thereby the condition of a surgical effect.

The complex impedance of tissue includes a resistance and a capacitance. Generally, tissue includes cells and fluid. Tissue resistance is created by the electrical conduction path through the fluid. Tissue capacitance is created by the cell membranes which provide an electrical insulating effect around the electrically conducting fluid within the cells. Cell membranes puncture/burst when a sufficient voltage is applied across the tissue. After the cell membrane bursts, the capacitive effect of the membrane is substantially reduced and the associated complex impedance of the tissue becomes more resistive and less capacitive. The complex impedance of the tissue is further changed when sufficient energy is dissipated in the tissue to vaporizes some of the fluid thereby causing an increase in resistance. Additional changes in the complex impedance are created through effects such as the denaturing and recombining of proteins in response to heating.

It has further been found that the complex impedance of the tissue can be measured over a time period to observe the extent, if any, of cellular membrane resealing. For example, cells which have not been destroyed by electrosurgical energy can reseal small holes in the cell membrane over a period of about a millisecond to a second. Measuring the change and rate of change of tissue's complex impedance in between or during delivery of electrosurgical energy provides information about the condition of the tissue and the associated surgical effect.

The present method for operating an electrosurgical unit includes controlling the delivery of energy to the tissue in response to the sensed tissue's complex impedance and/or rate of change of the complex impedance to provide improved surgical effects. More particularly, a sensor that uses an impedance controller for use with an electrosurgical generator to sense the complex impedance of the tissue is included in the present invention where the impedance controller regulates the output, for example the voltage that is converted to a RF signal, from the generator circuit in response to the change in the measured complex tissue impedance.

BRIEF DESCRIPTION OF THE DRAWINGS

For a more complete understanding of the present invention and further advantages thereof, reference is now made to the following Detailed Description, taken in conjunction with the Drawings, in which.

DETAILED DESCRIPTION OF THE INVENTION

Figure 1:
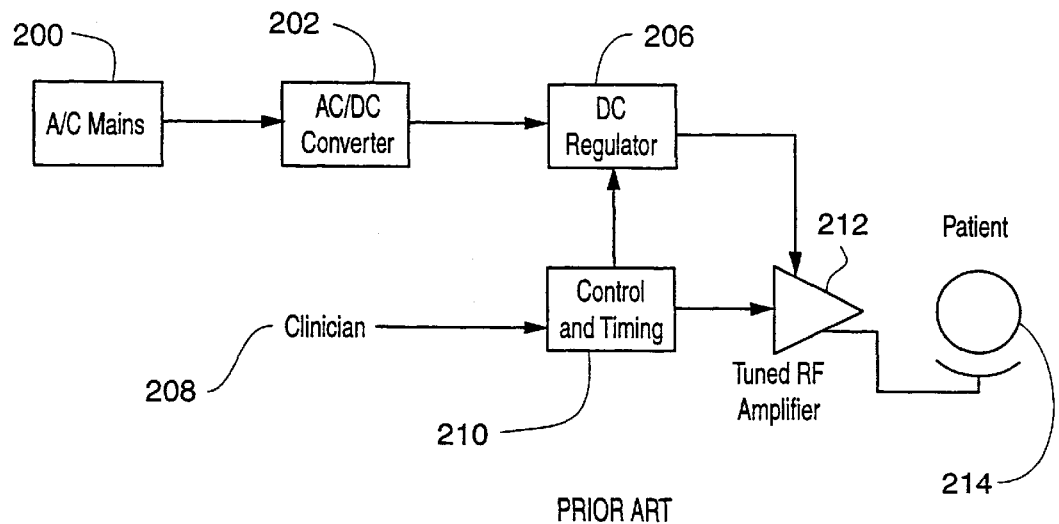
FIG. 1 is a prior art embodiment of an electrosurgical generator.
Figure 2:
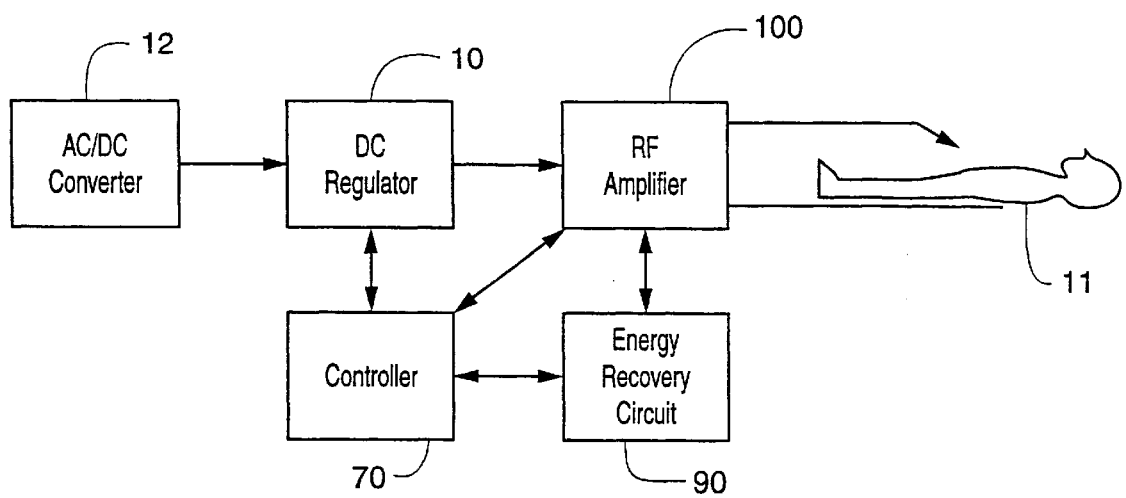
FIG. 2 is a block diagram illustrating the components of the generator.

Referring to FIG. 2, there is shown a block diagram of an electrosurgical generator constructed according to the principles of the present invention. The electrosurgical generator includes a DC regulator 10, an amplifier 100, an energy recovery circuit 90, and a controller 70.

The DC regulator 10 receives an input DC voltage from a power source 12 and converts the input DC voltage into an output DC voltage that is provided to the amplifier 100. The amplifier 100 converts the DC voltage from the regulator 10 into a radio-frequency output signal that is provided to a tissue mass 11. The energy recovery circuit 90 alternately stores energy from the amplifier 100 and releases energy back to the amplifier 100 to increase the efficiency at which energy is transferred from the power source 12 to the tissue 11. The controller 70 regulates the DC regulator 10, the amplifier 100, and the energy recovery circuit 90 to create a predetermined radio-frequency output signal from the electrosurgical generator that is operative for performing a desired electrosurgical operation, e.g., desiccation, fulguration, cutting, or cutting with hemostasis.

The inventive DC regulator 10 is described first. That description is followed by a description of the inventive amplifier 100 and then the inventive energy recovery circuit 90. Finally, a tissue impedance controller 109 (FIG. 9) is described that controls the flow of energy to the tissue in response to a sensed tissue condition to provide improved surgical effects.

Figure 3:
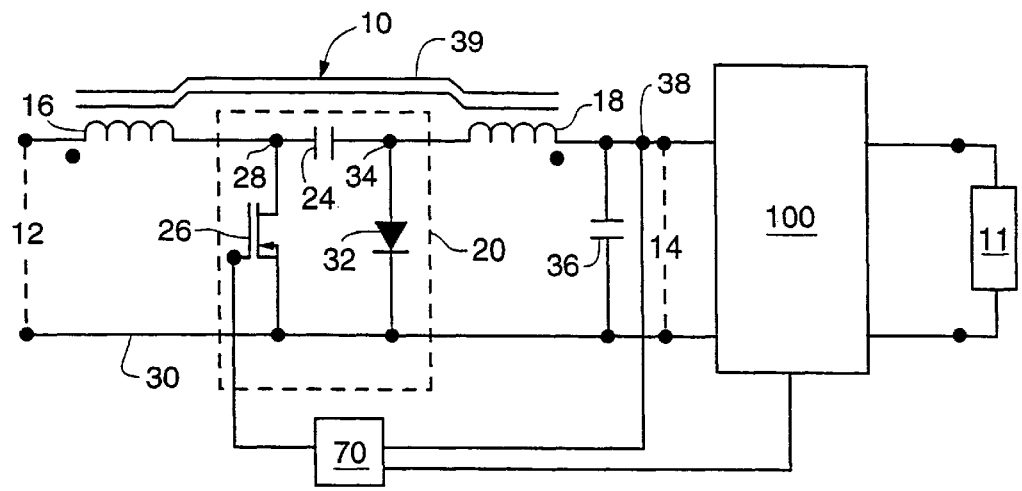
FIG. 3 is a schematic of a DC regulator embodiment according to the present invention.

In one aspect of the invention the DC regulator 10 (FIG. 3) converts an input DC voltage from the power source 12 to an output DC voltage that can be higher or lower than the first DC voltage. The DC regulator 10 achieves this conversion with a higher efficiency, a substantially reduced radiation of electromagnetic interference, and a lower number and smaller size of components than known electrosurgical generators.

The DC regulator 10 includes an input inductor 16 in series with the DC power source 12, an output inductor 18 in series with the amplifier circuit 100, and an energy transferring circuit 20. The energy transferring circuit 20 includes a storage capacitor 24, a switch 26 (e.g., insulated gate bipolar transistor) for alternately connecting (i.e., closed switch and disconnecting (i.e., open switch) a first junction 28 between the input inductor 16 and the storage capacitor 24 to a current return path 30 of the power source 12, and a diode 32 for alternately connecting (i.e., diode forward biased) and disconnecting (i.e., diode reversed biased) a second junction 34 between the storage capacitor 24 and the output inductor 18 to the current return path 30. A filter capacitor 36 is connected across the output of the DC regulator 10.

During the interval when the switch 26 is open, the diode 32 is forward biased and the capacitor 24 is charging through the input inductor 16 which reduces the input current ripple and radiated electromagnetic interference. During the interval when the switch 26 is closed, the capacitor 24 is connected across the diode 32, thereby reverse biasing the diode 32. The capacitor 24 discharges through the output inductor 18 and the amplifier 100. The output inductor 18 reduces the output current ripple and radiated electromagnetic interference. The switching cycle is then repeated by the switch 26 opening to forward bias the diode 32 and to recharge the capacitor 24 through the input inductor 16.

In this manner, the DC regulator 10 capacitively transfers energy from the power source 12 to the amplifier 100. Capacitive energy transfer is substantially more effective on a per unit size and weight basis than the inductive energy transfer used in prior electrosurgical generators. For example, a capacitor of 1 microfarad charged to 50 V has a stored energy of 1.25 mJ, equal to an inductor of 2.5 mH passing 1 A. The size of a 1 microfarad 50 V capacitor, however, is considerable smaller than a 2.5 mH 1 A inductor. Furthermore, capacitive energy transfer is more efficient than inductive energy transfer which has a relatively high loss of transferred energy due to resistive heating of the inductor.

The DC output voltage from the DC regulator 10 can be higher or lower than the DC input voltage from the power source 12 and is adjusted according to the following formula:

$$Voutput/Vinput = D/D'$$

where:

Voutput is the DC output voltage;

Vinput is the DC input voltage;

D is the fractional time that the switch 26 is closed (i.e., the time that the switch 26 is closed divided by the time for one cycle between the switch closing a first and then a second time); and D' is the fractional time that the switch is open (i.e., D'=(1−D)).

In this manner, the output voltage can be adjusted lower than the input voltage (step-down conversion) for D<0.5 or above the input voltage (step-up conversion) for D>0.5.

The controller 70 adjusts the output voltage by opening the switch 26 (i.e., biasing the transistor to achieve low impedance) and closing the switch 26 (i.e., biasing the transistor to achieve high impedance) according the formula above. The controller 70 in FIG. 3 performs current feedback control by sensing the output current at node 38 and adjusting the duty cycle of the switch 26 to maintain the voltage and/or current of the DC regulator 10 within a predetermined range to provide a desired surgical effect.

Energy dissipation in the switch is substantially eliminated by the controller 70 closing the switch 26 when substantially zero voltage and zero rate of change of voltage are present across the switch 26, thereby avoiding the simultaneous application of a voltage across the switch 26 and a current through the switch 26. The frequency at which the switch 26 can be operated under these zero voltage conditions can be increased by selecting the storage capacitor 24 and the inductors 16 and 18 to provide a rapid discharge of the capacitor 24 through the output inductor 18 and the amplifier 100.

In another embodiment, current ripple in the input inductor 16 and/or output inductor 18 is further reduced by magnetically coupling the inductors 16 and 18. Magnetic coupling 39 is provided by winding the inductors together on a magnetic core. With coupled inductors, energy transfers from the source to the load through the storage capacitor 24 (i.e., by the electric field) and directly through the coupled inductors 39 (i.e., by the magnetic field). The total DC magnetizing current in the magnetic core is the sum of the input and output currents. The turns ratio and coupling coefficient of the inductors 16 and 18 can be selected so that the current ripple in either, but not both, is reduced to zero.

Figure 4:
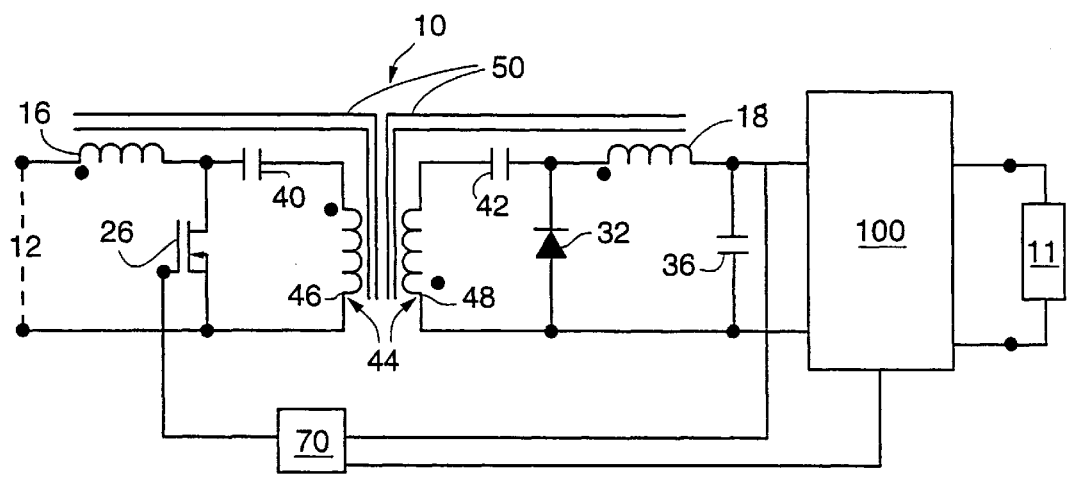
FIG. 4 is a schematic of an isolated DC regulator embodiment according to the present invention.

In electrosurgery it is advantageous to have DC isolation between a power source and the tissue/output load 11. Such isolation is advantageous, for example, due to the substantial variation in resistance of the tissue/output load 11 (e.g., varying from essentially zero to infinity). The present invention is easily extended to achieve such isolation. With reference now to FIG. 4, an embodiment is shown that achieves both isolation between the power source 12 and the amplifier circuit 100 and further reduction of the current ripple in the input and output current ripple. Isolation is provided by dividing the storage capacitor 24 of FIG. 3 into two capacitors 40 and 42 and interposing an isolation transformer 44 between them. The isolation transformer 44 includes a primary winding 46 and a secondary winding 48. One capacitor 40 is connected in series with the input inductor 16 and the primary winding 46. The other capacitor 42 is connected in series with the output inductor 18 and the secondary winding 48.

The inductors 16 and 18 and the isolation transformer 44 can be magnetically coupled 50 to reduce the input and output current ripple. Under certain conditions, both the input and output current ripple can be reduced to zero. The input current ripple can be reduced to zero under the following condition:

$$Le1 = L11\ [N2/N1 - 1]$$

where:
Le1 is the leakage inductance of the input inductor 16;
N1 is the number of turns of the input inductor 16;
N2 is the number of turns of the output inductor 18; and
L11 is the self-inductance of the input inductor 16.
Here, input ripple current may be reduced to zero by having N1, the number of winding turns in the input inductor, substantially equivalent to N2, the number of winding turns in the output inductor. In one embodiment, N1 and N2 need only be approximately equivalent to produce a reduction in the input current ripple.

The output current ripple can be reduced to zero under the following condition:

$$Le2 = L11\ (N2/N1)^2\ [N2/N1 - 1]$$

where:
Le2 is the leakage inductance of the output inductor 18;
N1 is the number of turns of the input inductor 16;
N2 is the number of turns of the output inductor 18; and
L11 is the self-inductance of the input inductor 16.
Similarly, the output ripple current may also be reduced to zero by having N2 substantially equivalent to N1. Again, in one embodiment N2 and N1 need only be approximately equal to produce a reduction in the output ripple current.

In another aspect of the invention an improved amplifier 100 is provided for converting the DC output voltage from the DC regulator 10 to a radio-frequency output signal provided to the tissue 11. The amplifier 100 achieves this conversion with high efficiency and substantially reduced radiation of electromagnetic interference.

Figure 5:
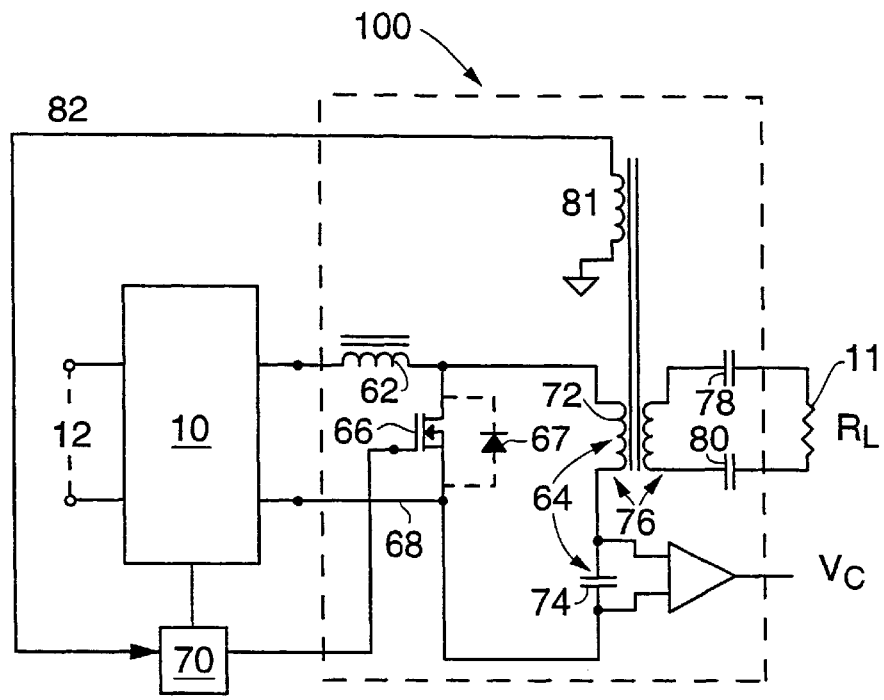
FIG. 5 is a schematic of an amplifier embodiment according to the present invention.

With reference now to FIG. 5, the amplifier 100 includes an input inductor 62 for reducing input current ripple, a resonant circuit 64 connected in series with the input inductor 62, and a transistor switch 66 for alternately connecting (closing) and disconnecting (opening) a current return path 68 of the amplifier 100 to a junction of the input inductor 62 and the resonant circuit 64.

The resonant circuit 64 generally includes an inductor 72, a capacitor 74, and the complex impedance of the tissue impedance 11. The controller 70 adjusts the frequency and magnitude of the radio-frequency output voltage of the amplifier 100 by opening the switch 66 (i.e., biasing the transistor to achieve low impedance) and closing the switch 66 (i.e., biasing the transistor to achieve high impedance). The controller 70 for the amplifier 100 can include simple oscillating circuits or a more complex feedback controller to regulate the switch 66.

As the switch 66 is cyclically operated by the switch controller 70, the input signal from the DC regulator 10 is converted into an output signal corresponding to the switching frequency. The magnitude and frequency of the output signal is regulated by adjusting the duty ratio the switch 66, i.e., adjusting the ratio of time that the resonant circuit 64 is charged to the total time over which the resonant circuit 64 is charged and discharged. During the time that the switch 66 is closed, the voltage across the switch 66 is essentially zero and the input current flows through the input inductor 62 to ground. The input inductor 62 is sufficiently large so as to act as a source of substantially constant current. When the switch 66 is opened, the input current flows through the resonant circuit 64. The transient response of the resonant circuit 64 is the response of a damped second-order system created by the series connection of the inductor 72, the capacitor 74, and the tissue impedance 11. Energy within the resonant circuit 64 is dissipated during a resonant transient across the resistive component of the tissue impedance 11. DC isolation is provided between the amplifier 100 and the tissue impedance 11 by an isolation transformer 76 and DC filter capacitors 78 and 80.

The efficiency of the amplifier 100 is enhanced by selecting the inductor 72 and capacitor 74 in the resonant circuit 64 to provide a damped response with zero voltage and zero rate of change of voltage across the switch substantially simultaneous to switch 66 closing. Zero voltage switching can further be enabled by an anti-parallel diode 67 connected across the switch 66. The anti-parallel diode 67 turns on for negative switch 66 current independent of the switch being open or closed, and hence more easily and automatically maintains the zero voltage switching described above.

In this manner, energy dissipation in the switch 66 is substantially eliminated by avoiding the simultaneous application of a voltage across the switch 66 and a current through the switch 66. The zero rate of change of voltage across the switch 66 substantially simultaneous to the switch closing permits an increased range of tissue impedances (i.e., a range of second order responses) for which zero voltage switching will be achieved.

According to another aspect of the present invention the operating condition of the output transformer can be sensed. Such optical sensing may be done using a sense winding 81 that provides a voltage signal 82 to controller 70.

According to yet another aspect of the present invention, an energy recovery circuit is provided for use in an electrosurgical generator to improve the efficiency of energy delivery to the tissue. The energy recovery circuit generally includes at least one energy storage device (e.g., capacitor, inductor, or combination thereof) and at least one switch (e.g., bipolar transistor, insulated gate bipolar transistor, or field effect transistor) that alternatively stores and releases electrical energy in the electrosurgical generator.

Figure 6:
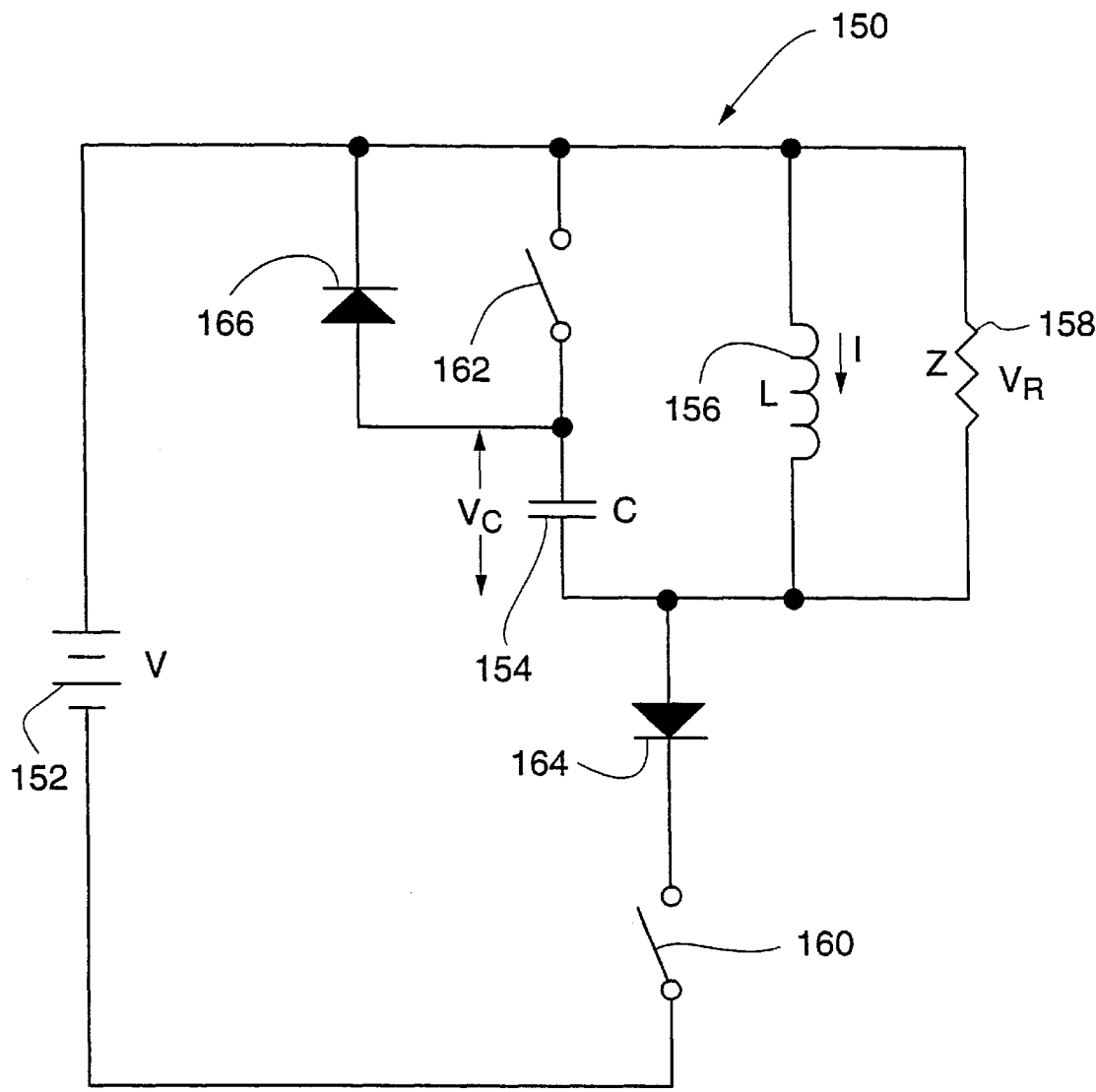
FIG. 6 is a schematic of one embodiment of an energy recovery circuit.

Referring to FIG. 6, an energy recovery circuit 150 is shown including inductive storage means 156, having inductance L, and capacitive storage means 154, having capacitance C, where both storage means are for storing electrical energy. In addition, circuit 150 also includes substantially DC power supply 152 having voltage V and resistive load 158 having a complex impedance Z that represents a patient. In operation, energy recovery circuit 150 has a state where first switch 160 is closed and inductor 156 is allowed to charge to a stored energy of $\frac{1}{2}LI^2$, where I is the current that passes through inductor 156. When first switch 160 opens inductor 156 transfers energy to capacitor 154 due to the action of diode 166. When diode 166 is conducting, second switch 162 may be closed. When second switch 162 is opened, all energy remaining in the circuit 150 will be stored in capacitor 154 rather than being dissipated as heat. When another energy delivery cycle is initiated, the voltage, $V_c$, across the capacitor 154 is measured and inductor 156 is charged with current where:

$$\text{Energy per period} = \frac{1}{2}LI^2 + \frac{1}{2}CV_c^2 + \int_o^\tau |V_R^2/Z| dt$$

where:

$V_R$ is the RMS voltage on the patient 158

$\tau$ is the period of an energy delivery cycle.

Therefore, the energy that was not dissipated from the circuit 150 and stored in capacitor 154 is used in the next energy delivery cycle rather than being dissipated as heat.

Figure 7:
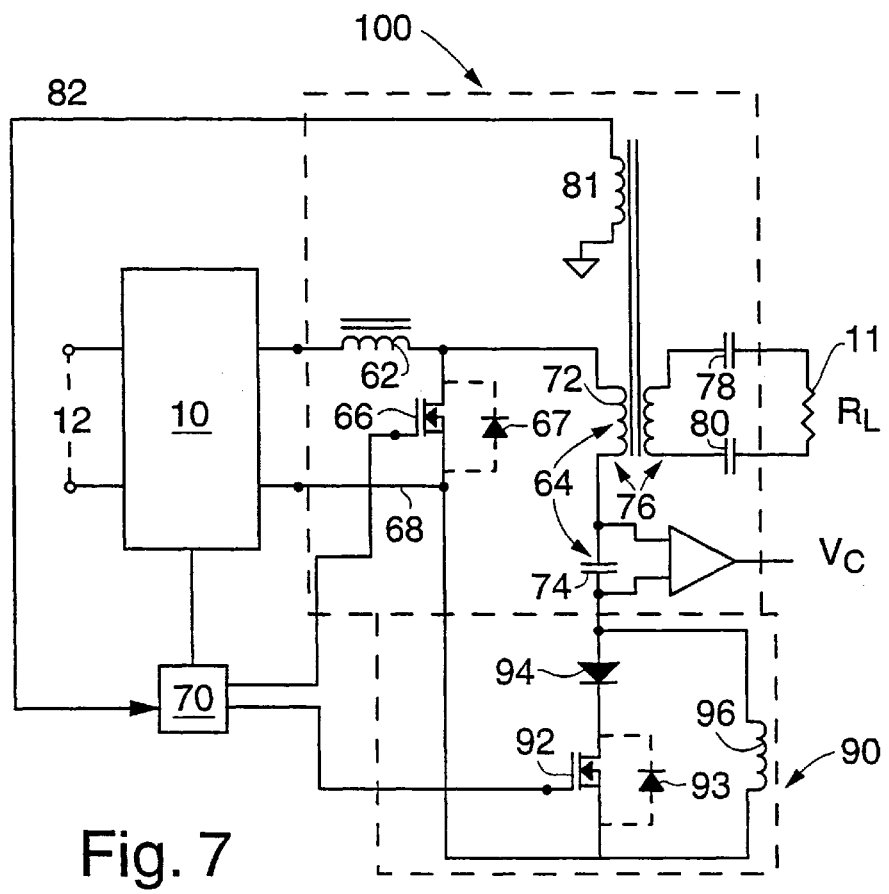
FIG. 7 is a schematic of an energy recovery circuit embodiment in combination with the amplifier of FIG. 5 according to the present invention.

With reference now to FIG. 7, an embodiment of an energy recovery circuit 90 is shown in combination with the amplifier 100 of FIG. 5. The use of an energy recovery circuit 90 in combination with the amplifier 100 of FIG. 5 is intended only to illustrate the operation of the energy recover circuit 90 and not to limit its use in combination with an amplifier 100. The energy recovery circuit 90 includes a transistor switch 92, an energy storage inductor 96, and a diode 94 in series with the amplifier 100 and in parallel with the energy storage inductor 96. The controller 70 regulates the switch 92 to selectively store and release energy between the energy recovery circuit 90 and the amplifier 100.

As previously described, the transient response of the output signal delivered by the amplifier 100 to the tissue impedance 11 for certain electrosurgical operations is that of a damped second-order system. Power within the resonant circuit 64 is transferred as a burst to the tissue that decays over a time constant defined by the inductor 72, the capacitor 74, and the impedance of the tissue 11. At the end of a burst from the amplifier 100, the energy that has not been transferred to the tissue 11 generally remains within the generator where it is dissipated as heat.

To avoid this loss of energy, the controller 70 stores some of the energy in the amplifier 100 by opening the switch 92 and passing the current through the energy storage inductor 96. At the end of a burst, when the controller 70 opens the amplifier switch 66, the controller 70 closes the switch 92 to trap the stored energy in a closed-circuit path connecting the energy storage inductor 96, the diode 94, and the switch 92. During a subsequent burst (i.e., after the controller 70 closes the amplifier switch 66), the controller 70 opens the switch 92, thereby transferring the energy remaining in the energy storage inductor 96 to the amplifier 100. Power dissipation in the switch 92 is minimized by including an anti-parallel diode 93 across the switch 92. The anti-parallel diode 93 turns on for negative voltages across the switch 92 to assist in obtaining zero voltage switching of the switch 92.

In this manner, energy is selectively stored and released between the energy recovery circuit 90 and the amplifier 100 to increase the efficiency of energy transfer to the tissue. The energy recovery circuit 90 provides the further advantage of rapidly damping the output power of the generator at the end of a pulse.

Figure 8A:
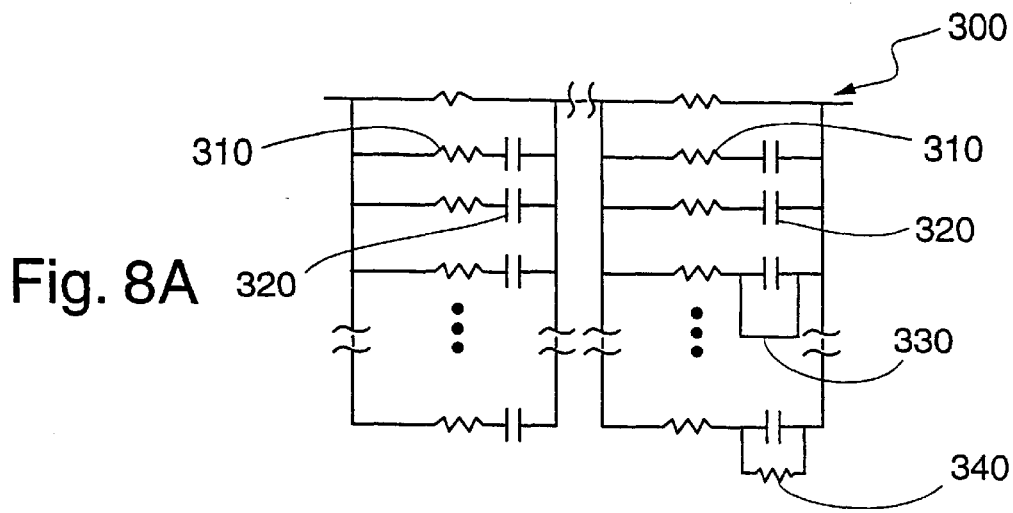
FIG. 8a is a distributed complex tissue impedance model of a tissue sample.
Figure 8B:
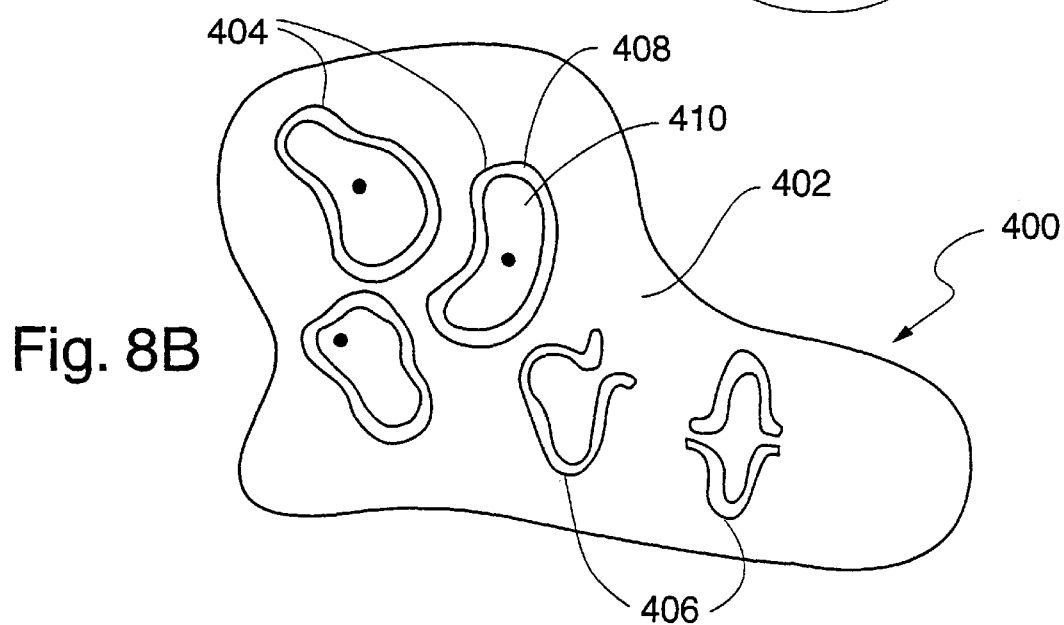
FIG. 8b is a sample of a tissue structure.

Referring to FIGS. 8a and 8b, the present inventors believe a distributed complex tissue impedance model may be obtained from a tissue structure that is undergoing an electrosurgical procedure. More particularly, the complex impedance 300 of tissue 400 includes a resistance 310 and a capacitance 320. Generally, tissue 400 includes cells, 404 and 405, and fluid 402. Tissue resistance 310 is created by the electrical conduction path through the fluid 402. Tissue capacitance 320 is created by the cell membranes 408 which provide an electrical insulating effect around the electrically conducting fluid 410 within the cells. Cell membranes puncture/burst, as shown by 406, when a sufficient voltage is applied across the tissue 400. After the cell membrane bursts 406, the capacitive effect of the membrane 406 is substantially reduced, as shown by short circuit 330, and the associated complex impedance 300 of the tissue 400 becomes more resistive and less capacitive. The complex impedance 300 of the tissue 400 is further changed when sufficient energy is dissipated in the tissue 400 to vaporize some of the fluid 402 thereby causing an increase in resistance, as shown by the additional resistor 340. Additional changes in the complex impedance 300 are created through effects such as the denaturing and recombining of proteins in response to heating.

It has further been found that the complex impedance of the tissue can be measured over a time period to observe the extent, if any, of cellular membrane resealing. For example, cells which have not been destroyed by electrosurgical energy can reseal small holes in the cell membrane over a period of about a millisecond to a second. Measuring the change and rate of change of tissue's complex impedance in between or during delivery of electrosurgical energy provides information about the condition of the tissue and the associated surgical effect.

Figure 9:
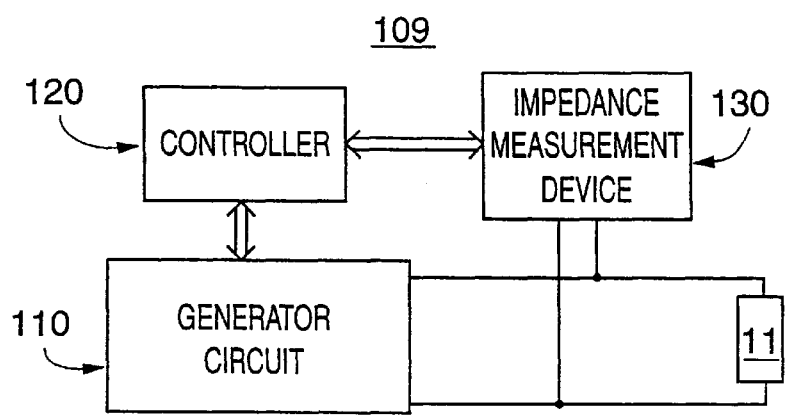
FIG. 9 is a block diagram of an tissue impedance controller according to the present invention.

With reference now to FIG. 9, a tissue impedance controller 109 for use in an electrosurgical generator is illustrated according to another aspect of the present invention. The tissue impedance controller 109 includes a generator circuit 110, an impedance measurement device 130, and a controller 120 responsive to the impedance measurement device 130. The generator circuit 110 synthesizes radiofrequency pulses that are applied across tissue to produce electrosurgical effects. The impedance measurement device 130 measures the complex impedance of the tissue 11. The controller 120 regulates the generator circuit 100 in response to the measured tissue complex impedance 11 and the rate of change of impedance to provide improved electrosurgical effects.

In one embodiment as shown in FIG. 9, tissue impedance 11 is measured in between electrosurgical pulses. Between electrosurgical pulses, the controller 120 regulates the generator circuit 110 to apply a predetermined measurement signal across the tissue 11 for use by the impedance measurement device 130. The impedance measurement device 130 measures the complex impedance of the tissue 11 (i.e., by dividing the voltage signal across the tissue by the current through the tissue). The controller 120 analyzes the measured impedance and/or the rate of change of the measured impedance over a predetermined time period to determine the present condition of the tissue 11. The controller 120 compares the present tissue condition with a desired surgical effect and regulates the generator circuit 110 to obtain the desired surgical effect.

In another embodiment, tissue impedance is measured periodically or continuously during electrosurgical pulses. The impedance measurement device 130 applies a predetermined frequency voltage across the tissue 11 that has a different frequency than the signals synthesized by the generator circuit 110 for electrosurgical effects. The impedance measurement device 130 measures the current through the tissue 11 at the predetermined frequency to determine the complex impedance of the tissue 11 and thereby the tissue condition. The controller 120 then regulates the generator circuit 110 in response to the measured tissue condition to obtain a desired surgical effect.

The DC regulator 10, the amplifier 100, and the energy recovery circuit 90 of the present invention are each advantageous for use in the present generator circuit 110. The DC regulator 10 and the amplifier 100 enable the controller 120 to rapidly vary the characteristics of the output signal, including frequency, magnitude, and pulse width in response to the measured tissue complex impedance 11. The complex tissue impedance 11 can be more rapidly and accurately measured in between pulses by the energy recovery circuit 90 which efficiently captures the energy remaining in the generator circuit 110 at the end of a pulse and thereby rapidly dampens the output signal from the generator circuit 110 and allows rapid application of an impedance measurement signal to the tissue 11.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An electrosurgical generator for use in the performance of a surgical operation on a tissue mass, comprising:

a signal generating means adapted to apply electrosurgical output pulses across a tissue mass at a predetermined frequency;

impedance measuring means which measures at least one of a complex impedance and a rate of change of the complex impedance across the tissue mass through the application of a predetermined measurement signal across the tissue mass only between said electrosurgical output pulses; and control means which regulates the signal generating means based at least in part on said at least one of the complex impedance and rate of change of the complex impedance.

2. The electrosurgical generator of claim 1, wherein said predetermined measurement signal is at a different frequency than the electrosurgical output pulses.

3. The electrosurgical generator of claim 1, wherein the measurement includes measuring both of said complex impedance and the rate of change of the complex impedance across the tissue mass, and wherein the regulation is based on both of said measured complex impedance and measured rate of change of the complex impendence.

4. The electrosurgical generator of claim 1, wherein the impedance measuring means measures said complex impedance by dividing a voltage applied across the tissue mass by a current passing through the tissue mass.

5. The electrosurgical generator of claim 1, wherein the control means regulates a voltage output by said signal generating means based on said at least one of the complex impedance and rate of change of the complex impedance.

6. The electrosurgical generator of claim 1, wherein said at least one of the complex impedance and rate of change of the complex impedance corresponds with a tissue condition which is compared with a desired condition.

7. The electrosurgical generator of claim 1, said signal generating means including:

(a) dc regulator means for converting a first dc signal from a power source into a second dc signal having a predetermined voltage, including:

inductive input means for reducing current ripple in the first dc signal, capacitive energy storage means for storing and releasing energy, switch means for alternatively charging said capacitive energy storage means with the first dc signal and discharging said capacitive energy storage means to generate the second dc signal, and inductive output means for reducing current ripple in the second dc signal;

(b) amplifier means for converting the second dc signal into the output signal having a predetermined frequency;

wherein said control means provides control signals to at least one of the dc regulator means and said amplifier means to establish at least one of said predetermined voltage and said predetermined frequency.

8. The electrosurgical generator of claim 7, said amplifier means comprising:

an amplifier input inductor for reducing current ripple of the second dc signal;

a resonant circuit connectable across the tissue mass, wherein said resonant circuit is connected in series with said amplifier input inductor and includes an inductor and a capacitor; and amplifier switch means for alternately connecting and disconnecting a current return path of said amplifier means to a junction between said input inductor and said resonant circuit thereby providing an output signal.

9. The electrosurgical generator of claim 8, wherein said inductor and said capacitor of said resonant circuit are selected to provide a substantially zero voltage across said amplifier switch means and a substantially zero instantaneous rate of change of voltage across said amplifier switch mans prior to said connecting by said amplifier switch means thereby substantially reducing energy dissipation by said amplifier switch means.

10. The electrosurgical generator of claim 1, said signal generating means including:
(a) dc regulator means for converting a first dc signal from a power source into a second dc signal having a predetermined voltage;
(b) amplifier means for converting the second dc signal into the output signal into the output signal having predetermined frequency, including:
an input inductor for reducing current ripple in the second dc signal,
a resonant circuit connectable across the tissue mass, wherein said resonant circuit is connected in series with said input inductor and includes an inductor and a capacitor; and
switch means for alternately connecting and disconnecting a current return path of said amplifier to a junction between said input inductor and said resonant circuit;
wherein said control means for establishes at least one of said predetermined voltage and said predetermined frequency.

11. The electrosurgical generator of claim 10, wherein said inductor and said capacitor of said resonant circuit are selected so as provide a substantially zero voltage across said switch means and a substantially zero instantaneous rate of change of voltage across said switch means prior to said connecting by said switch means thereby substantially reducing energy dissipation by said switch means.

12. The electrosurgical generator of claim 10, further comprising:
energy recovery means electrically connected to said resonant circuit for selectively storing and releasing energy of output signal.

13. The electrosurgical generator of claim 1, wherein the control means regulates at least one of a voltage output, frequency, and pulse width of said electrosurgical output pulses in response to said at least one of the complex impedance and rate of change of the complex impedance.

14. An electrosurgical generator for providing an output signal for use in the performance of a surgical operation on a tissue mass comprising:
a signal generating means adapted to apply electrosurgical output pulses across a tissue mass including:
(a) dc regulator means for converting a first dc signal from a power source into a second dc signal having a pre-determined voltage;
(b) amplifier means for converting the second dc signal into an output signal having a predetermined frequency; and,
(c) energy recovery means electrically connected to said amplifier means for selectively storing and releasing energy of the output signal;

impedance measuring means which measures at least one of a complex impedance and a rate of change of the complex impedance across the tissue mass through the application of a predetermined measurement signal across the tissue mass only between said electrosurgical output pulses; and
control means which regulates the signal generating means based at least in part on said at least one of the measured complex impedance and measured rate of change.

15. The electrosurgical generator of claim 14, said energy recovery means including:
energy storage means electrically connected to said amplifier means; and
energy recovery switching means, in connection with said control means, to alternately direct excess energy from the amplifier means to the energy recovery storage means and to return the excess energy from the energy storage means to the amplifier means.

16. The electrosurgical generator of claim 15, wherein the energy storage means is an inductor.

17. The electrosurgical generator of claim 15, wherein the energy recovery means comprises a transistor.

18. The electrosurgical generator of claim 15, said amplifier means including:
an amplifier input inductor for reducing current ripple of the second dc signal;
a resonant circuit connectable across the tissue mass, wherein said resonant circuit is connected in series with said amplifier input inductor and includes an inductor and a capacitor; and
amplifier switch means for alternately connecting and disconnecting a current return path of said amplifier means to a junction between said input inductor and said resonant circuit thereby providing an output signal.

19. The electrosurgical generator of claim 18, the energy recovery means including:
energy storage means in connection with said resonant circuit;
energy recovery switching means in connection with the control means, which alternately directs excess energy from the resonant circuit to the energy recovery storage means, and return the excess energy to the amplifier means.

20. The electrosurgical generator of claim 14, wherein said energy recovery means captures energy from the amplifier means at the end of each of said electrosurgical output pulses.

* * * * *